US00PP27051P3

(12) United States Plant Patent
Chapman

(10) Patent No.: US PP27,051 P3
(45) Date of Patent: Aug. 9, 2016

(54) *ZOYSIA JAPONICA* L.×*ZOYSIA TENUIFOLIA* L. PLANT NAMED 'BK-9'

(50) Latin Name: ***Zoysia japonica* L.×*Zoysia tenuifolia* L.**
Varietal Denomination: BK-9

(71) Applicant: Sod Solutions, Inc., Mount Pleasant, SC (US)

(72) Inventor: John Chapman, Foley, AL (US)

(73) Assignee: Sod Solutions, Inc., Mount Pleasant, SC (US)

( * ) Notice: Subject to any disclaimer, the term of this patent is extended or adjusted under 35 U.S.C. 154(b) by 127 days.

(21) Appl. No.: 14/120,305

(22) Filed: May 14, 2014

(65) Prior Publication Data

US 2015/0020273 P1 Jan. 15, 2015

Related U.S. Application Data

(60) Provisional application No. 61/855,426, filed on May 15, 2013.

(51) Int. Cl.
*A01H 5/12* (2006.01)

(52) U.S. Cl.
USPC ..... Plt./390
CPC ..... *A01H 5/12* (2013.01)

(58) Field of Classification Search
USPC ..... Plt./390
See application file for complete search history.

(56) References Cited

PUBLICATIONS https://www.youtube.com/watch?v=yCwSPIjaxH8. Oct. 2, 2011.*

* cited by examiner

*Primary Examiner* — Annette Para
(74) *Attorney, Agent, or Firm* — Myers Bigel & Sibley, P.A.

(57) ABSTRACT

A new and distinct variety of *Zoysia* grass named 'BK-9', is characterized by its short and narrow leaf blade, small inflorescences, fast lateral growth and recovery rate and improved cold hardiness, compared to other *Zoysia* grass varieties.

6 Drawing Sheets

Latin name of the genus and species: The Latin name of the genus and species of the novel variety disclosed herein is *Zoysia japonica* L.×*Zoysia tenuifolia* L. and therefore characterizes a cross between two species of *Zoysia*.

Variety denomination: The inventive variety of *Zoysia japonica* L×*Zoysia tenuifolia* L. disclosed herein has been given the variety denomination 'BK-9'.

BACKGROUND OF THE INVENTION

The present invention relates to a new and distinct perennial variety of *Zoysia japonica* L.×*Zoysia tenuifolia* L.

'BK-9' (also referred to herein as Geo) is the result of a selection done on a *Zoysia* production field by a sod producer named Craft Farms. The selection was made in 2006. The parent grasses are unknown and therefore are not named. The field which originated 'BK-9' was established from progeny selections made in the late 80's. The progenies were derived from crosses made between *Zoysia japonica* L. and *Zoysia tenuifolia* L. Parents for these crosses were selected from sources that had had good cold hardiness, shade tolerance and overall quality. Plants (progenies) originated from these crosses were selected based on desirable characteristics such as open habit of growth, fine texture and speed of growth. These plants (F2) were re-evaluated and the plants with the best cold hardiness and overall quality were selected and planted on a new field in Southern Alabama. This second field of selections was called 'BK-7'. In the summer of 2006 a new selection was made on the 'BK-7' field based on superior cold hardiness, early spring green up, intense green color, fine texture, high shade tolerance and rapid re-growth after harvesting. This new selection was called 'BK-9'. After being selected, 'BK-9' has been vegetatively propagated in Alabama near Foley. Being a fast lateral growing *Zoysia* grass with fine texture is one of the reasons that makes 'BK-9' a unique and different type of *Zoysia*; other characteristics that makes 'BK-9' unique are excellent cold hardiness, excellent shade tolerance and improved grass quality. It is anticipated that the plant of this invention will be marketed under the synonym Geo as a trade name. 'BK-9' is so identified in pictures and morphological and agronomic charts of this disclosure.

SUMMARY OF THE INVENTION

'BK-9' is a distinctive variety of *Zoysia japonica* L.×*Zoysia tenuifolia* L. having a brilliant green (10GY 5/4 on a Munsell Color Chart), fine leaf and stolon texture, small inflorescence, fast lateral growth, superior low temperature tolerance adaptation and excellent shade tolerance. 'BK-9' is a very poor seed producer, making it suitable for vegetative reproduction only, such as sprigs, rhizomes, plantlets, or sod. 'BK-9' is adapted for use in the hot-humid, and transition zone areas in the US, zones 6b to 9 of the Plant Heat Zone Map.

DESCRIPTION OF THE NEW VARIETY

The following is a detailed description of the new grass variety, based upon observations of the plant grown in field plots at a research area located near Starkville, Miss. 'BK-9' is an outstanding *Zoysia* grass cultivar with fine texture, improved shade tolerance and quick lateral speed of growth. 'BK-9' recovers very quickly after harvesting, regenerating a mature field in about half of the time compared to other fine bladed *Zoysias*. Its fast recovery from wear make it suited for use on sports fields and golf. 'BK-9' has an improved cold hardiness exhibiting little winter damage and winter-kill after the winter, making it suitable for use in the transition zone. 'BK-9' has excellent shade tolerance requiring only 3 to 4 hours of sunlight to maintain good quality and color. 'BK-9' can only be established vegetatively by sprigs, rhizomes, plugs or sod. Its bright green color (10GY 5/4 on a Munsell Color Chart) and fine texture give it a highly appealing turf-grass quality and appearance.

Dimensions of Morphological Structures

'BK-9' was compared to 3 other cultivars of *Zoysia* grass in a study planted near Starkville, Miss. starting in August 2010. The three cultivars chosen for comparison were 'Meyer', 'SS-Z15' and 'El Toro' because the parents of 'BK-9' are unknown and therefore a comparison to a parent was not possible.

Figure 1:
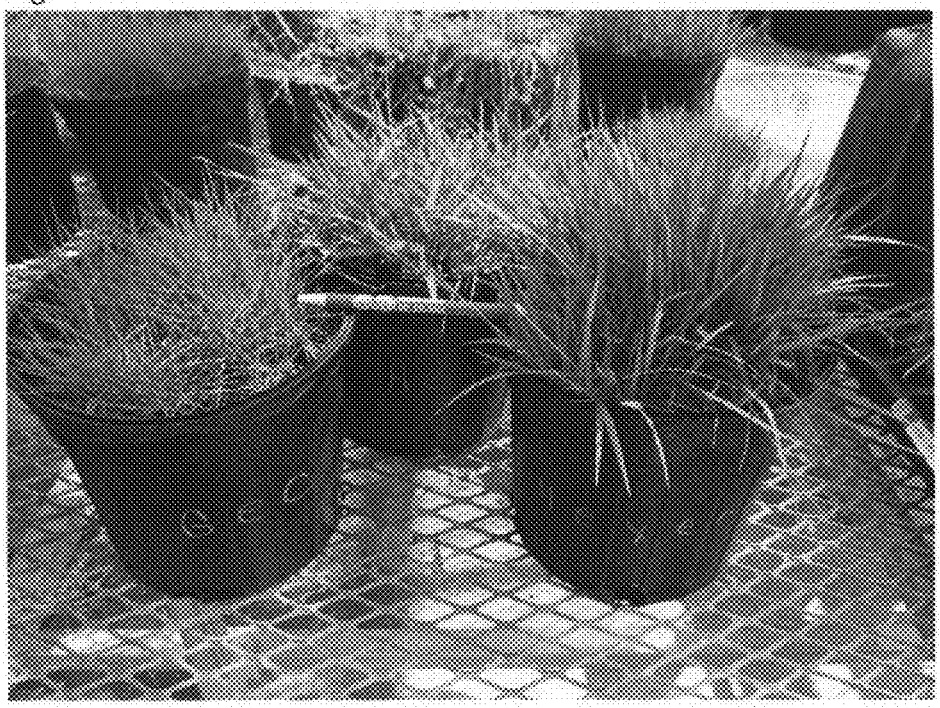
FIG. 1: 'BK-9' (Geo) planted in pots at green-house in a research area: Starkville, Miss.
Figure 2:
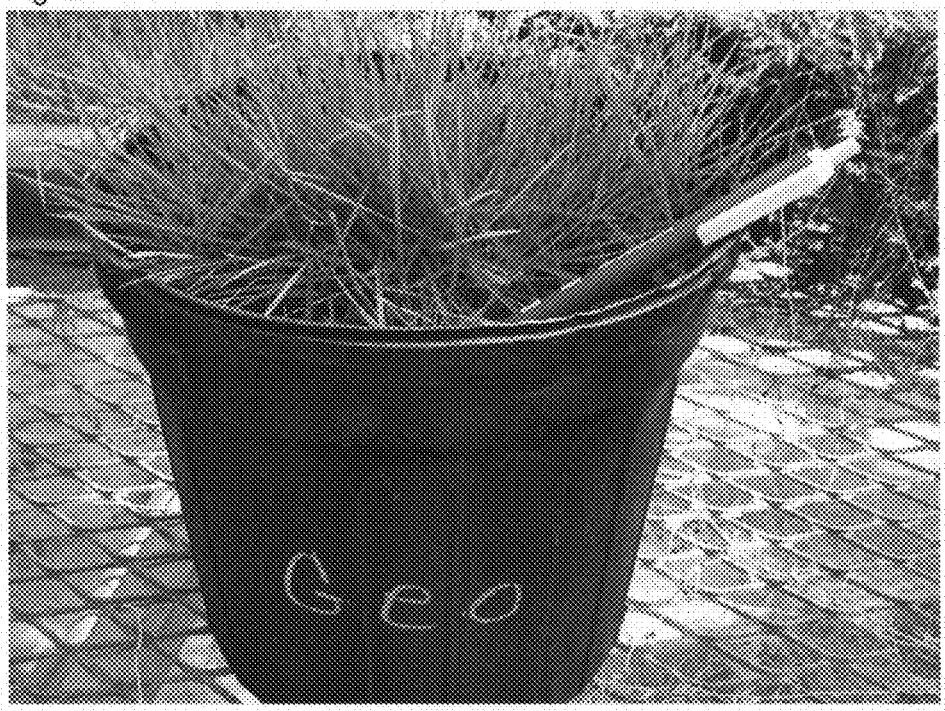
FIG. 2: 'BK-9' (Geo) pot for evaluation inside a greenhouse near Starkville, Miss.

Each variety was planted in 1 gallon pots, using potting mix: Redi-earth Plug and Seedling Mix (Sungro Horticulture, Bellevue, Wash.) and were kept at a green-house to produce plant material for morphological evaluations. FIG. 1 shows 'BK-9' and Meyer *Zoysia* as grown in one gallon pots with 'BK-9' on the left. FIG. 2 shows a gallon pot of 'BK-9' during evaluation. Plant material was collected using a completely random experiment design with 4 replications (pots). Green-house complex had natural sunlight conditions. The pots were allowed to grow for 4 weeks, and then were clipped once to encourage density and stolon development. They were allowed to grow un-mowed for another 4 weeks before measurement. The leaf blade measurements were conducted from Aug. 26-Oct. 7, 2010. Seventy randomly selected leaf blades from each cultivar were measured for length and width. Width was measured at the widest point of the blade. The internode measurements were conducted from Nov. 1-12, 2010. All the stolons that grew off each pot were used to measure the internode diameter and internode length. The inflorescence measurements were conducted from Dec. 14, 2010-Mar. 2, 2011. Twenty five seed-heads were randomly selected from each cultivar. Three florets were randomly selected from each head for measurement.

The Analysis of Variance (ANOVA) indicated that cultivars differed significantly for most variables measured (Table 1).

TABLE 1

Analysis of Variance for Zoysia grass cultivars comparisons with '13K-9' conducted during the 2010 and 1011 growing seasons.

| | Mean Squares of the traits | | | | |
|---|---|---|---|---|---|
| Source | ID (mm) | IL (mm) | LL (mm) | LW (mm) | TIL (mm) |
| Variety | 12.1** | 1986.9** | 20231.6** | 1128.4** | 34684.1** |
| Error | 0.09 | 69.30 | 316.81 | 0.203 | 187.6 |
| CV | 17.18 | 34.60 | 23.99 | 12.63 | 14.61 |

| | Mean Squares of the traits | | | |
|---|---|---|---|---|
| Source | FRL (mm) | PL (mm) | NSI | SL (mm) |
| Variety | 2854.8** | 17989.1** | 2265.6** | 9.42* |
| Error | 12.28 | 161.8 | 21.15 | 0.06 |
| CV | 13.91 | 18.56 | 19.56 | 8.58 |

ID - Internode Diameter, IL - Internode Length, LL - Leaf Length (mm), LW - Leaf Width (mm), TIL - Total Inflorescence Length, FRL - Floral Region Length, PL - Peduncle Length, NSI - Number of Spikelets per Inflorescence, SL - Spikelet Length.
*Significant at 5% level
**Significant at 1% level Cultivars showed significant differences on many of the analyzed morphological characteristics (Table 1). Internode Diameter (ID), Internode Length (IL), Leaf Length (LL), Leaf Width (LW), Total Inflorescence Length (TIL), Floral Region Length (FRL), Peduncle Length (PL) and Number of Spikelets per Inflorescence (NSI) were significantly different at 1% level (Table 1). Spikelet Length (SL) was significantly at 5% level (Table 1). The evaluations were well conducted and produced reliable results as demonstrated by the low Coefficients of Variation (CV) (Table 1).

Figure 3:
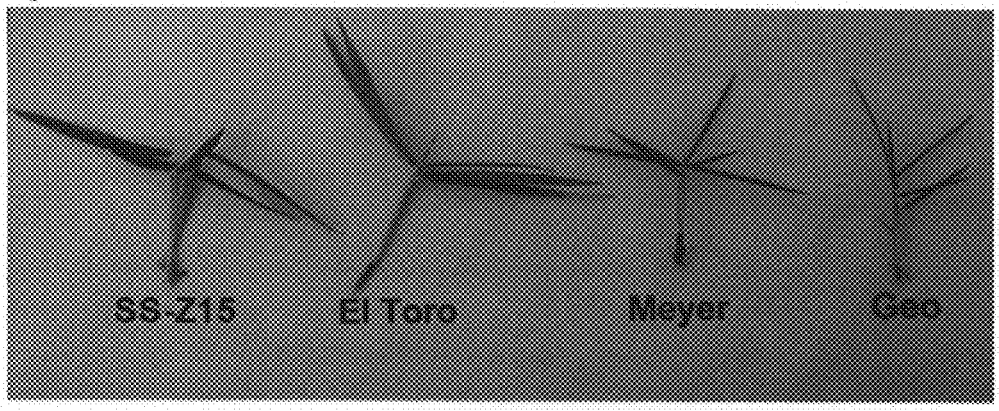
FIG. 3: Leaf detail of 'BK-9' (Geo) and other varieties.

In comparison to 'Meyer' and 'El Toro', the new variety, 'BK-9', has a finer texture because it has narrower leaves, shorter leaves and smaller internode diameter. 'BK-9' has a smaller leaf blade length (48.8 mm) when compared to 'Meyer' and the other varieties used as comparisons (Table 2). 'Meyer' is the variety that looks more similar to 'BK-9' using the naked eye, being that both varieties are considered to have a 'fine texture' (FIG. 3). 'Meyer', 'SS-Z15' and 'El Toro' have significantly longer leaf blades compared to 'BK-9'. Leaf blade lengths for 'Meyer', 'SS-Z15' and 'El Toro' were 84.4, 83.4 and 80.1 mm, respectively, while 'BK-9' leaf blade length was nearly half (48.8 mm) of those (Table 2). 'BK-9' also has the narrower leaf blade width (2 mm) among the tested varieties (Table 2) with 'Meyer's' leaf blade width being 3.0 mm and 'El Toro''s leaf blade width being 4.2 mm. 'BK-9' has a smaller internode diameter (1.4 mm) when compared to 'Meyer''s internode diameter (1.6 mm) and when compared to 'El Toro''s internode diameter (2.0 mm). Thus, while 'Meyer' had the second narrowest leaf blade width (Table 2), it was still significantly different than 'BK-9'. The leaf blade width difference between the two varieties was 1 mm; which is greater than 0.2 mm, the least significant difference (LSD) at 5% level (Table 2).

TABLE 2

*Zoysia* cultivar comparisons with 'BK-9' conducted during 2010.

| | Internode | | Leaf Blade | |
|---|---|---|---|---|
| Cultivar | Diameter (mm) | Length (mm) | Width (mm) | Length (mm) |
| 'SS-Z15' | 2.2 | 25.8 | 5.1 | 83.4 |
| El Toro | 2 | 30.2 | 4.2 | 80.1 |
| 'BK-9' | 1.4 | 23.3 | 2 | 48.8 |

TABLE 2-continued

*Zoysia* cultivar comparisons with 'BK-9' conducted during 2010.

| | Internode | | Leaf Blade | |
|---|---|---|---|---|
| Cultivar | Diameter (mm) | Length (mm) | Width (mm) | Length (mm) |
| Meyer | 1.6 | 18 | 3 | 84.4 |
| LSD(0.05) | 0.1 | 2.6 | 0.2 | 5.9 |

Figure 4:
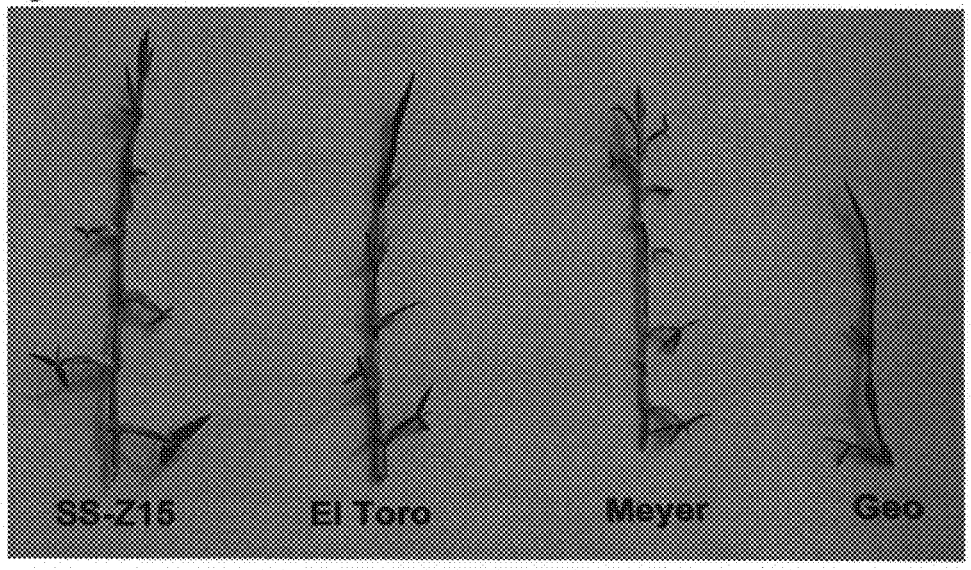
FIG. 4: Stolon detail of 'BK-9' (Geo) and other varieties.

'BK-9' has a dark purple stolon, similar to 'El Toro', while 'SS-Z15' and 'Meyer' have light green stolons (FIG. 4). Other distinctive characteristics of 'BK-9' are its small diameter and short internode. Table 2 shows that among the tested varieties, 'Meyer' has the shortest internode length (18.3 mm) and 'BK-9' has the second shortest internode length (23.3 mm). The difference between 'Meyer' and 'BK-9' (5.3 mm) was statistically different at 1% level (Table 1). 'BK-9' also exhibits the smallest internode diameter (1.4 mm), when compared to 'SS-Z15', 'El Toro' and 'Meyer' (Table 2). 'Meyer' exhibited the second smallest internode diameter (1.6 mm), which was still statistically different from 'BK-9' (0.20 mm) at the 5% level (Table 2).

Narrow and short leaf blades, combined with small internode diameter and short internode length (Table 2), allow 'BK-9' to exhibit a fine and dense aesthetic look. Normally, fine bladed *Zoysias* are spiked to the touch, making it unpleasant to step on or lie on top of. Despite having fine blades and short internodes, 'BK-9' is soft to the touch, providing a pleasant feeling when stepped on and touched.

Furthermore, the short and narrow leaf blades (Table 2) of 'BK-9' results in less scalping when maintained with a rotary mower, when other so called 'fine bladed' *Zoysias* have to be maintained with a reel mower to avoid scalping, due to their longer and wider leaf blades.

Figure 5:
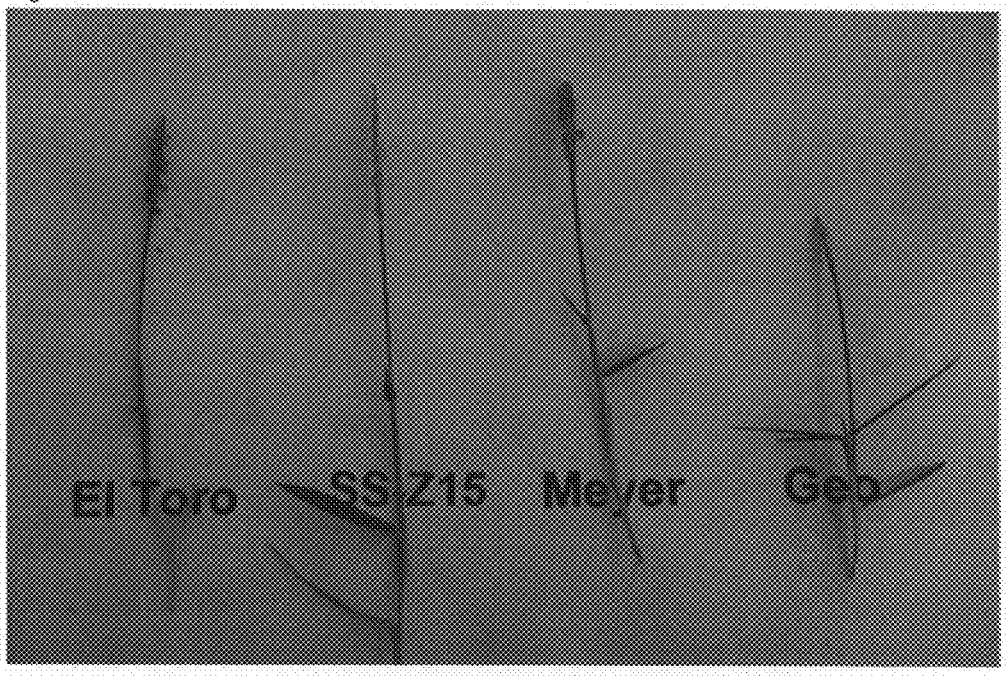
FIG. 5: Inflorescences of 'BK-9' (Geo) and other varieties of *Zoysia*.

In addition, 'BK-9' differs from 'Meyer' and 'El Toro' because it has smaller flowers (smaller total inflorescence length, smaller floral region length and smaller peduncle length) than 'Meyer' and 'El Toro'. 'BK-9' has small inflorescences (42.3 mm) when compared to total inflorescence length for 'Meyer' and 'El Toro' of 90.7 mm and 117.3 mm, respectively. In particular, 'BK-9' has short seed-heads (floral region) and peduncles (FIG. 5) compared to other *Zoysia* varieties. 'BK-9' floral region length is smaller (11.8 mm) when compared to the floral region length for 'Meyer' of 21.9 mm and for 'El Toro' of 31.1 mm. Further, 'BK-9' has a smaller peduncle length (30.5 mm) when compared to the peduncle length of 'Meyer' and 'El Toro' of 68.9 mm and 86.1 mm, respectively.

Figure 6:
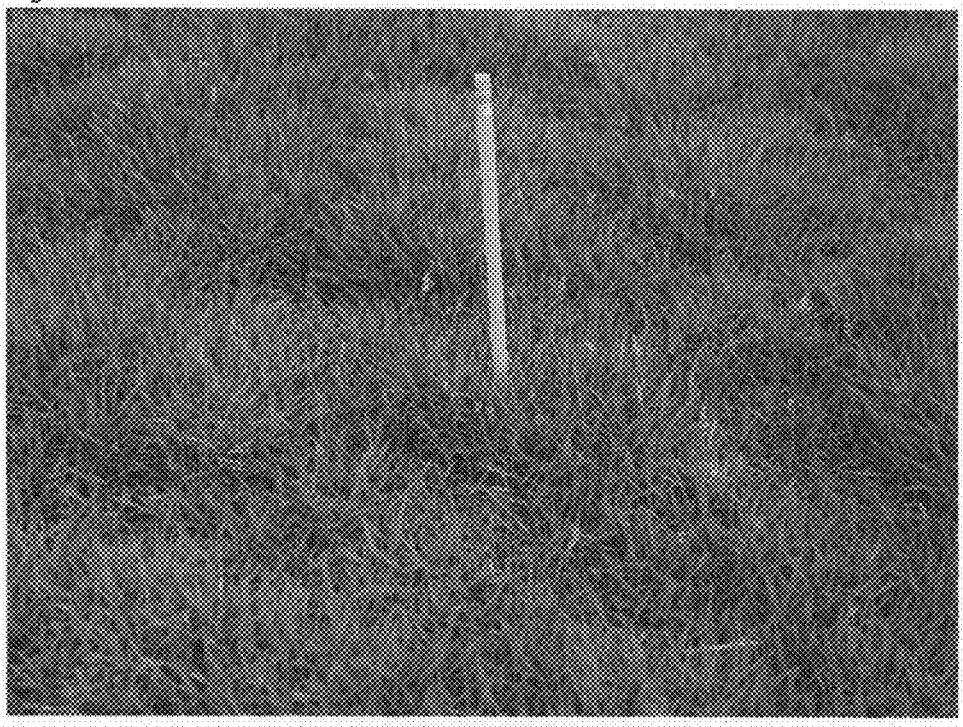
FIG. 6: 'BK-9' field showing flower structures blended in the canopy.

The total inflorescence structure of 'BK-9' easily hides in the plant canopy, making it difficult to see by a person walking the field. FIG. 6 shows 'BK-9' inflorescences blended into the grass canopy. The result is a grass field having a more pleasant look-with the predominant color being green from the leaves and not the purple color from the floral structure.

In addition to having the smallest total inflorescence among the compared varieties, 'BK-9' also exhibits the smallest number of spikelets per inflorescence (9.5) and spikelet length (2.3 mm) as shown in Table 3. 'El Toro' and 'SS-Z15' had a significant longer spikelet: 3.0 and 3.7 mm, respectively; while 'Meyer' had a spikelet length (2.6 mm) closer to that of 'BK-9'. Despite that, the difference between 'Meyer' and 'BK-9''s spikelet lengths (0.3 mm) was greater than the LSD at 5% (0.1 mm) as shown in Table 3 and therefore is statistically different.

TABLE 3

*Zoysias* inflorescences compared to 'BK-9' conducted in 2010.

| Cultivar | Total inflorescence length [a] mm | Floral region length [b] mm | Peduncle length [c] mm | Number of spikelets per inflorescence [d] | Spikelet length [e] mm |
|---|---|---|---|---|---|
| 'SS-Z15' | 124.7 | 36.0 | 88.7 | 25.5 | 3.7 |
| El Toro | 117.3 | 31.1 | 86.1 | 29.6 | 3.0 |
| Meyer | 90.7 | 21.9 | 68.9 | 29.4 | 2.6 |
| 'BK-9' | 42.3 | 11.8 | 30.5 | 9.5 | 2.3 |
| LSD(0.05) | 7.7 | 2 | 7.1 | 2.6 | 0.1 |

[a] Total inflorescence length is the mean of 25 observations per cultivar including the floral region and peduncle.
[b] Floral region length is the mean of 25 observations per cultivar
[c] Peduncle length is the mean of 25 observations per cultivar measured from the base of the floral region to the first node.
[d] Number of spikelets per inflorescence is the mean of 25 observations per cultivar determined by count.
[e] Spikelet length is the mean of 3 observations per inflorescence and 75 per cultivar

Growth Habits

Lateral Growth

Figure 7:
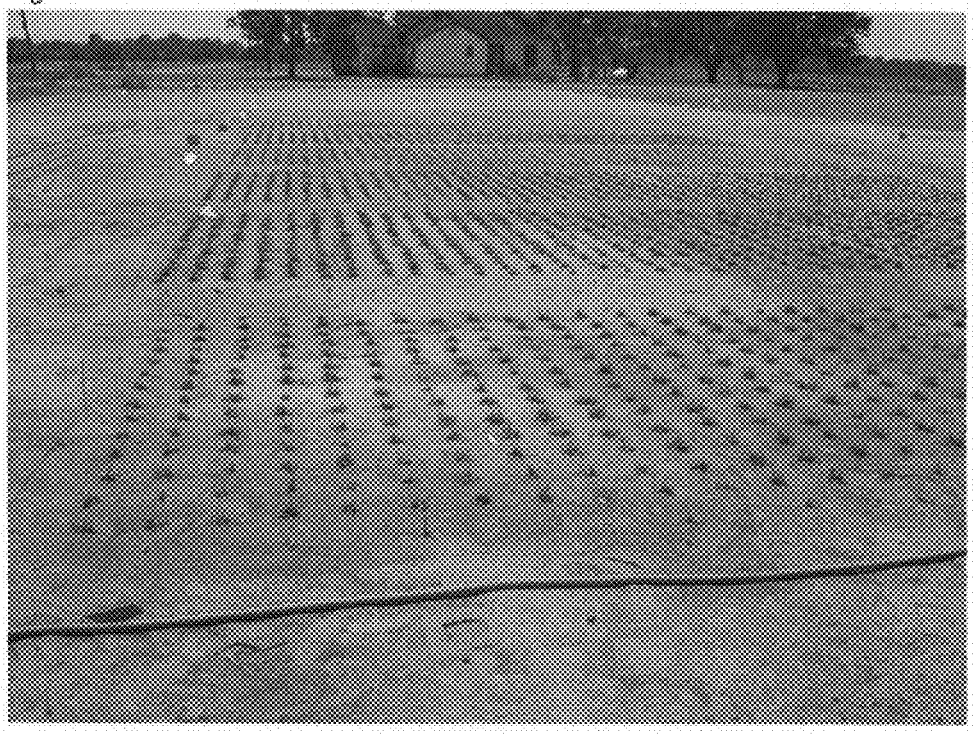
FIG. 7: Test plots with 'BK-9' and other experimental *Zoysias* near E. Bernard Tex.
Figure 8:
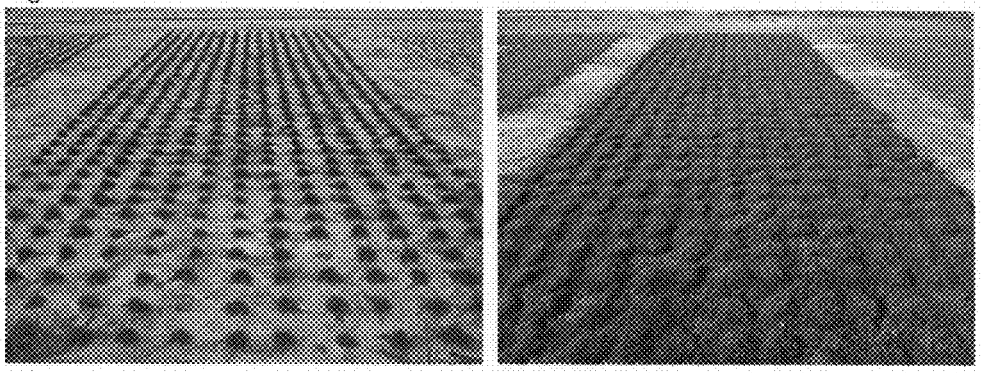
FIG. 8: 'BK-9' test plots near E. Bernard, Tex.

A comparison study was installed in a private research company near East Bernard, Tex. in Jul. 15, 2009 to evaluate the speed of lateral growth of 'BK-9' and other experimental varieties of *Zoysia* (see, FIG. 7 and FIG. 8). All entries were planted using plugs produced in 72 cell trays. Plugs were planted in 10×30 ft. plots, using 12 inch centers. Plots were fertilized with 10 lbs. of 10-05-05/1000 sq. ft. spread immediately after planting the plugs, and watered in. Irrigation was applied at least once a week, until plugs were fully grown in, Experimental varieties included: 'Z-2', 'BK-9', 'SS-12', 'SS-13', 'Aloysia' and 'SS-Z15' (FIG. 7). Evaluations of percentage of ground covered (%) by the varieties and visual quality ratings (1 to 9, with 9=highest quality) were collected from July to October of 2009 (Tables 4 and 5).

TABLE 4

Ground cover of experimental Zoysias planted in 2009; near E. Bernard,TX.

| | Ground cover (%) | | | | | |
|---|---|---|---|---|---|---|
| Varieties | 8/26 | 9/5 | 9/15 | 9/25 | 10/6 | 10/22 |
| 'SS-Z15' | 25 | 30 | 30 | 40 | 60 | 85 |
| Aloysia | 30 | 40 | 50 | 85 | 80 | 90 |
| 'SS 12' | 45 | 60 | 90 | 95 | 95 | 97 |
| 'SS 13' | 30 | 50 | 65 | 80 | 90 | 95 |
| 'BK-9' | 40 | 45 | 50 | 80 | 90 | 100 |
| 'Z-2' | 40 | 50 | 60 | 70 | 80 | 95 |

Note:
Jul. 15, 2009 to Oct. 22, 2009 = 109 days.

'BK-9' grows faster than other varieties of *Zoysia*. 'BK-9' was the first variety to reach 100% of ground cover (Table 4), and the variety with the best average visual quality ratings (8.17) recorded along the tested period (Table 5). Normally, fine bladed *Zoysias* such as 'Emerald', 'Cavalier' or 'Diamond', take 14 months or more to cover the ground after planting. These varieties also take, in average, the same amount of time to recover after harvesting and regenerate a field back to be harvestable again. 'BK-9' has demonstrated in a production field situation that can regrow back in 6-8 months after harvesting.

TABLE 5

Quality Ratings of experimental Zoysias, 2009, planted near E. Bernard, TX.

| | Quality Visual Ratings (1-9) | | | | | | |
|---|---|---|---|---|---|---|---|
| Varieties | 8/26 | 9/5 | 9/15 | 9/25 | 10/6 | 10/22 | Average |
| 'SS-Z15' | 6 | 7 | 8 | 6 | 8 | 8 | 7.17 |
| Aloysia | 6 | 7 | 8 | 8 | 8 | 8 | 7.50 |
| 'SS 12' | 7 | 7 | 7 | 7 | 8 | 8 | 7.33 |
| 'SS 13' | 7 | 7 | 6 | 8 | 7 | 8 | 7.17 |
| 'BK-9' | 6 | 8 | 9 | 9 | 9 | 8 | 8.17 |
| 'Z-2' | 7 | 7 | 7 | 8 | 8 | 8 | 7.50 |

9 = Best possible rate

Fast regrowth is an important, unique and desirable characteristic for a fine bladed *Zoysia*. It allows 'BK-9' to be produced on average, more than once a year; reducing its production cost and as a consequence making the market price more affordable for the end user. The fact that 'BK-9' grows from plugs to 100% cover (FIG. 8), in 109 days (Table 4), indicates that it can regenerate a production field after harvesting more quickly than other fine bladed *Zoysias*.

Cold Tolerance

Figure 9:
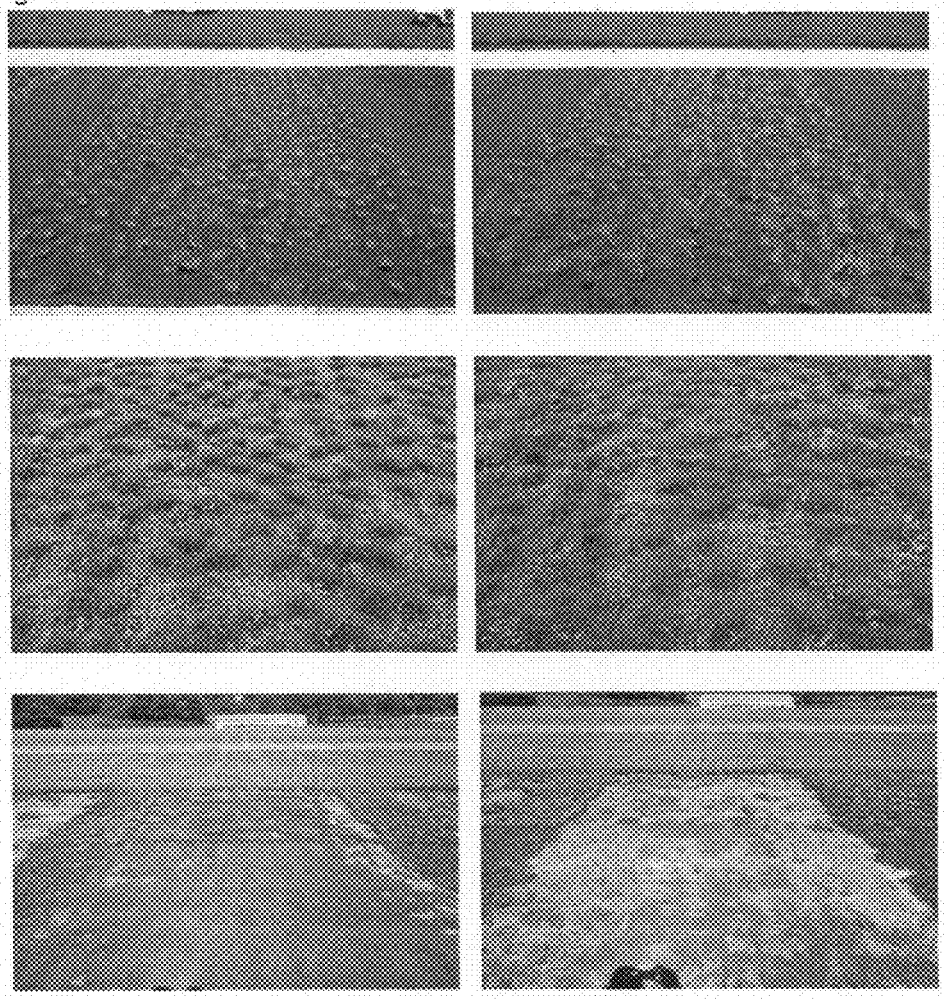
FIG. 9: Test plots with 'BK-9' near Lexington, Ky.

'BK-9' has less winter kill and faster spring green up when compared to other varieties of *Zoysia*. In order to evaluate the cold tolerance of 'BK-9' and the amount of winter damage it sustain when used in the transition zone of the United States (Zone 7 and 6b USDA Plant Hardiness Zone Map), a replica of the experiment planted in central Texas was planted in a sod producer area near Raeford, N.C. (Zone 7) and in a private research company near Lexington, Ky. (Zone 6b) (see, FIG. 9). Test plots were the same size as in Texas (10×30 ft.), planted with plugs using the same methodology, i.e. 12 inches center and identical fertilization regime. Test plots in North Carolina were planted in April 2009 and were planted in June 2009 in Kentucky (FIG. 9).

Test plots near Lexington, Ky. provided the best information about cold hardiness and winter damage on 'BK-9' because the research was located on the southern part of Hardiness Zone 6, with average minimum temperatures ranging for −10 to 0 F. Plots were planted on late spring of 2009 and maintained throughout the growing season with good nutrition and irrigation. After the 2009/2010 winter, plots were evaluated with visual ratings for % of winter kill, spring green up and overall quality (Table 6).

TABLE 6

Evaluations on experimental *Zoysias* planted near Lexington, KY.

| | Visual Ratings | | |
|---|---|---|---|
| Varieties | Winter kill (%) | Spring Green-up (1-9) | Overall Quality (1-9) |
| 'SS-Z15' | 5 | 5 | 5 |
| Aloysia | 7 | 6 | 6 |
| 'SS 12' | 4 | 3 | 4 |
| 'SS 13' | 2 | 4 | 4 |
| 'BK-9' | 8 | 7 | 8 |
| 'Z-2' | 4 | 4 | 5 |

9 = Best possible rate

Results showed that 'BK-9' exhibit the least winter kill (8/9), the best spring green-up (7/9) and overall quality (8/9) among the tested varieties (Table 6). FIG. 9 shows the evolution of two entries planted near Lexington, Ky.: 'BK-9' on the left column and 'SS-12' on the right column. The first row shows entries right after planting on June 2009, the second row shows pictures of the entries taken in September 2009 and the third and last row are pictures of the entries taken in the following summer, June 2010. Both entries ('BK-9' and 'SS-12') had a good establishment (first row of FIG. 9) and development during the growing season (second row of FIG. 9). However, after the 2009/2010 winter, the 'SS-12' entry suffered substantial winter kill (4/9—Table 6) while 'BK-9' had close to zero winter kill (8/9—Table 6). In addition, 'BK-9' had an early and uniform green-up (7/9—Table 6) compared to 'SS-12' (3/9—Table 6); resulting in a better overall quality for 'BK-9' (8/9—Table 6) over 'SS-12' (4/8—Table 6). The low winter kill, uniform green-up and best overall quality of 'BK-9' can be visualized on the third and last row of FIG. 9.

That which is claimed is:

1. A new and distinct variety of *Zoysia* grass named 'BK-9', as herein illustrated and described, characterized by its distinctive and unique combination of several characteristics such as: short and narrow leaf blade, small inflorescences, fast lateral growth and recovery rate and improved cold hardiness.

* * * * *